US009883850B2

(12) United States Patent
Monahan et al.

(10) Patent No.: US 9,883,850 B2
(45) Date of Patent: Feb. 6, 2018

(54) ASSESSMENT OF RIGHT VENTRICULAR FUNCTION USING CONTRAST ECHOCARDIOGRAPHY

(71) Applicant: Vanderbilt University, Nashville, TN (US)

(72) Inventors: Kenneth J. Monahan, Nashville, TN (US); Evan Brittain, Nashville, TN (US); Steven M. Boronyak, Nashville, TN (US); William David Merryman, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 314 days.

(21) Appl. No.: 14/315,737

(22) Filed: Jun. 26, 2014

(65) Prior Publication Data

US 2015/0005629 A1    Jan. 1, 2015

Related U.S. Application Data

(60) Provisional application No. 61/839,594, filed on Jun. 26, 2013, provisional application No. 61/977,344, filed on Apr. 9, 2014.

(51) Int. Cl.
     *A61B 8/08*      (2006.01)
     *G06T 7/00*      (2017.01)

(52) U.S. Cl.
     CPC ............ *A61B 8/481* (2013.01); *A61B 8/0883* (2013.01); *A61B 8/5223* (2013.01); *G06T 7/0016* (2013.01); *G06T 2207/10016* (2013.01); *G06T 2207/10132* (2013.01); *G06T 2207/30048* (2013.01); *G06T 2207/30104* (2013.01)

(58) Field of Classification Search
CPC ..... A61B 8/481; A61B 8/065; A61B 5/02028; A61B 5/0263; A61K 49/223
See application file for complete search history.

(56) References Cited

U.S. PATENT DOCUMENTS

| | | | | |
|---|---|---|---|---|
| 5,302,372 A | * | 4/1994 | Lin | ...................... A61K 49/223 424/9.52 |
| 5,685,310 A | * | 11/1997 | Porter | ..................... A61B 8/481 600/453 |
| 5,797,396 A | * | 8/1998 | Geiser | ..................... G06T 7/602 382/128 |
| 7,819,806 B2 | * | 10/2010 | Yang | ..................... A61B 5/1075 600/437 |
| 8,308,644 B2 | * | 11/2012 | McMorrow | .............. A61B 8/08 600/437 |
| 9,320,491 B2 | * | 4/2016 | Konofagou | .......... A61B 8/0883 |

(Continued)

*Primary Examiner* — Baisakhi Roy
(74) *Attorney, Agent, or Firm* — Tarolli, Sundheim, Covell & Tummino LLP

(57) ABSTRACT

Systems and methods are provided for determining a right ventricular transit time for a patient. An echodense contrast is injected into a patient. A first representative region, representing the right ventricle of the patient, is selected. A second representative region, representing the bifurcation of the main pulmonary artery, is selected. Respective first and second time series of intensity values for the first and second representative regions are generated via echocardiography. The right ventricular transit time is determined from the first and second time series of intensity values. The right ventricular transit time is displayed to a user.

19 Claims, 4 Drawing Sheets

(56) References Cited

U.S. PATENT DOCUMENTS

| | | | |
|---|---|---|---|
| 2001/0021371 A1* | 9/2001 | Eriksen | A61B 8/06 424/9.52 |
| 2003/0153823 A1* | 8/2003 | Geiser | G06T 7/0012 600/407 |
| 2003/0199934 A1* | 10/2003 | Struble | A61N 1/36564 607/17 |
| 2005/0085707 A1* | 4/2005 | Maria Korsten | A61B 8/481 600/407 |
| 2006/0161062 A1* | 7/2006 | Arditi | A61B 8/06 600/443 |
| 2010/0168554 A1* | 7/2010 | Sorensen | A61B 5/029 600/420 |
| 2011/0286645 A1* | 11/2011 | Hautvast | G06T 7/0014 382/128 |
| 2013/0325110 A1* | 12/2013 | Khalil | A61F 2/2463 623/2.11 |
| 2014/0171795 A1* | 6/2014 | Eggers | A61B 5/02028 600/432 |

* cited by examiner

ASSESSMENT OF RIGHT VENTRICULAR FUNCTION USING CONTRAST ECHOCARDIOGRAPHY

RELATED APPLICATIONS

This application claims priority from U.S. Provisional Application Nos. 61/839,594, filed Jun. 26, 2013 and 61/977,344, filed Apr. 9, 2014, both entitled ASSESSMENT OF RIGHT VENTRICULAR FUNCTION USING CONTRAST ECHOCARDIOGRAPHY, the subject matter of which is incorporated herein by reference in its entirety.

TECHNICAL FIELD

This invention relates to medical diagnostic systems, and more particularly, to systems and methods for assessing right ventricular function using contrast echocardiography.

BACKGROUND

Right heart dysfunction is associated with poor outcomes in patients with valvular disease, cardiomyopathy, diastolic dysfunction, and pulmonary arterial hypertension, as well as patients having recent heart transplants. Conversely, preserved right ventricular function, even in the setting of elevated pulmonary arterial pressure, is associated with improved survival, decreased hospitalization, and improved exercise capacity in patients with chronic heart failure. Early diagnosis of right ventricular dysfunction could lead to more effective treatment and, ultimately, better outcomes.

SUMMARY OF THE INVENTION

In accordance with an aspect of the present invention, a method is provided for determining a right ventricular transit time for a patient. An echodense contrast agent is injected into a patient. A first representative region, representing the right ventricle of the patient, is selected. A second representative region, representing the bifurcation of the main pulmonary artery, is selected. Respective first and second time series of intensity values for the first and second representative regions are generated via echocardiography. The right ventricular transit time is determined from the first and second time series of intensity values. The right ventricular transit time is displayed to a user.

In accordance with another aspect of the present invention, a method is provided for determining a transit time for a patient. An echodense contrast agent is injected into a patient. First and second representative regions are selected. Respective first and second time series of intensity values are generated for the first and second representative regions via echocardiography. At least one inflection point is located in each of the first and second time series of intensity values. The transit time is determined from the at least one inflection point located in each of the first and second time series of intensity values and displayed to a user.

In accordance with yet another aspect of the present invention, a system is provided for non-invasive evaluation of right ventricular function using contrast-enhanced echocardiography. An ultrasound assembly is configured to image a region containing at least the right ventricle and the bifurcation of the main pulmonary artery to provide a first time series of intensity values representing the right ventricle and a second time series of intensity values representing the first branch of the main pulmonary artery. A parameter calculation component is configured to determine at least a right ventricular transit time (RVTT) from the first and second time series of intensity values. A modeling component is configured to provide a parameter representing the right ventricular function of the patient from at least the determined RVTT. An output device is configured to provide the parameter provided by the modeling component to a user in a human comprehensible form.

In accordance with still another aspect of the present invention, a method is provided for determining a transit time for a patient. An echodense contrast agent is injected into a patient. First and second representative regions are selected. Respective first and second time series of intensity values for the first and second representative regions are generated via echocardiography. A point of largest change is located in each of the first and second time series of intensity values. The point of largest change represents a time, m, that minimizes the following function of m:

$$MSE(m) = \sum_{i=1}^{m}\left(I_i - \frac{\sum_{i=1}^{m} I_i}{m}\right)^2 + \sum_{i=m+1}^{n}\left(I_i - \frac{\sum_{i=m+1}^{n} I_i}{n-m}\right)^2 \quad \text{Eq. 1}$$

In this function, n is an number of intensity values in a given time series and $I_i$, is an $i^{th}$ intensity value in the given time series. The transit time is determined from the point of largest change located in each of the first and second time series of intensity values and displaying to a user.

DETAILED DESCRIPTION

In accordance with an aspect of the present invention, a non-invasive and reproducible method of assessing the function of the right ventricle is provided. The complex morphology of the right ventricle and its location adjacent to the chest wall make thorough assessment of global right ventricular function via echocardiography difficult. Due to these limitations, ejection fraction, the clinical gold standard measurement of left ventricular function, cannot be accurately measured in the right ventricle by echocardiography. Surrogate measures of RV function such as Tricuspid Annular Plane Systolic Excursion, Right ventricular Index of Myocardial Performance, and tissue Doppler imaging are often employed as adjuncts to 2-D echocardiography, but are not ideal because their measurement is dependent on high quality images and adequate alignment with the ultrasound beam. In addition, these parameters vary based on cardiac loading conditions. Other options include cardiac MRI and right-heart catheterization. However, the former is expensive and not widely available and the latter is invasive and carries the inherent attendant risks.

Figure 1:
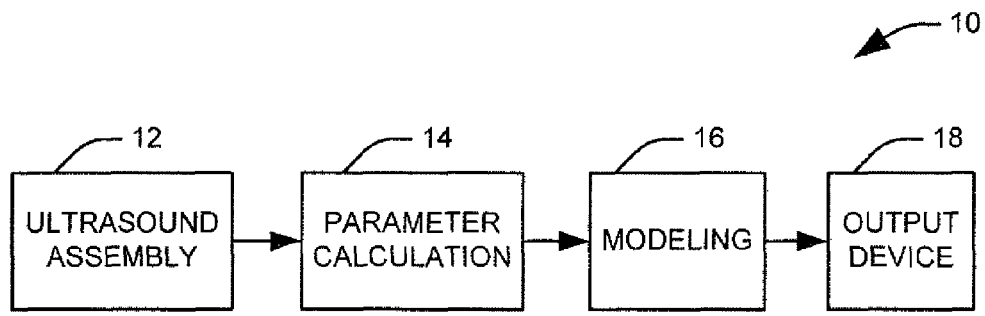
FIG. 1 illustrates a system for non-invasive evaluation of right ventricular function using contrast-enhanced echocardiography in accordance with an aspect of the present invention.

To this end, FIG. 1 illustrates a system 10 for non-invasive evaluation of right ventricular function using contrast-enhanced echocardiography in accordance with an aspect of the present invention. Specifically, the system 10 is configured to calculate at least a right ventricle transit time, that is, the amount of time that it takes blood to pass from the right ventricle to the first branch point (bifurcation) of the main pulmonary artery, as a metric for evaluating right ventricular function. The system 10 uses an echodense contrast agent, such as Definity or Optison, to facilitate this measurement.

The system 10 includes an ultrasound assembly 12 configured to image a region containing at least the right ventricle and the bifurcation of the main pulmonary artery. Specifically, the ultrasound assembly 12 is positioned with respect to a patient as to image at least a first representative region within the right ventricle and a second representative region at the bifurcation of the main pulmonary artery. In one implementation, the first representative region can be located between one and two millimeters from the coaptation point of the tricuspid valve and centered between the right ventricular free wall and the interventricular septum. In some applications, a third representative region can be provided in the left atrium as well to facilitate calculation of a pulmonary transit time (PTT). For example, the third representative region can be located one centimeter posterior to the mitral annulus and centered between the lateral left atrial wall and the interatrial septum. Accordingly, the ultrasound assembly 12 can provide intensity values over time for the first and second regions of interest. It will be appreciated that, when the representative regions are larger than one pixel, the intensity value for the regions can be an average (e.g., mean or median) of the intensity values of the individual pixels.

The determined intensity values are provided to a parameter calculation component 14 that determines at least a right ventricular transit time (RVTT) from the ultrasound intensity values. It will be appreciated that, when the echodense contrast agent is within a representative region, the intensity of the reflected ultrasound signal from that region will increase noticeably. The parameter calculation component 14 can be fully automated or can utilize an associated user interface in guiding a user in the calculation of the RVTT. In the illustrated implementation, the parameter calculation component 14 is implemented as machine readable instructions on a non-transitory computer readable medium, but it will be appreciated that the parameter calculation component can also be implemented as dedicated hardware (e.g., an application specific integrated circuit [ASIC] or a field programmable gate array [FPGA]) or a combination of software and dedicated hardware.

In one implementation, the parameter calculation component 14 can analyze a time series of intensity values for each representative region to determine a time interval between peak intensities of the first and second representative regions, representing the RVTT. Alternatively, a time at which the intensity exceeds a threshold value at a given representative region can be determined to be a "time of first appearance" for the contrast agent at that region, and the RVTT can be calculated as a time interval between the times of first appearance of the first and second representative regions. In still another implementation, inflection points representing a rise in signal intensity are determined from a time series of intensity values, with the RVTT determined from the inflection points. Methods for determining a transit time via location of inflection points is discussed in detail in FIGS. 4-6 below.

In one implementation, multiple time intervals can be determined, for example, via repeated contrast injections, representing multiple transits of contrast agent through the right ventricle, and one of a median value, a mean value, and a weighted combination of the determined values can be utilized for the RVTT. In another implementation, a time interval between peak intensities of the first and third representative regions can be determined to provide a PTT. Each of the RVTT, the PIT, and a ratio of the RVTT to the PTT can be calculated and provided to a modeling component 16.

The inventors have determined that a prolonged RVTT is indicative of right ventricular dysfunction. Accordingly, the modeling component 16 is configured to evaluate the right ventricular function of a patient based on at least one of the RVTT and the RVTT/PVT ratio to provide a parameter representing the right ventricular function. It will be appreciated that this evaluation can be diagnostic, where the parameter output from the modeling component 16 represents a likelihood that a patient currently has a particular defect in right ventricular function, such as an impairment in RV ejection fraction. Alternatively, the evaluation can be prognostic, with the output parameter representing the likelihood of a particular outcome in a given time frame or an expected time before a particular outcome. The predicted outcome can include, for example, a general diagnosis of heart disease, a specific cardiac disorder, death, or a need for a heart transplant. Further, it will be appreciated that the modeling component 16 can utilize additional relevant features associated with the patient, such as parameters representing systolic and diastolic function of the left ventricle, age, sex, medical history, family history, weight, height, and blood pressure.

The modeling component 16 can be implemented as any appropriate classification or regression model, such as a polynomial model provided via least squares regression procedure, an artificial neural network, a statistical classifier, a support vector machine, or a comparable model. Such a model can be trained on a set of calculated right ventricle transit times validated by existing methods, such as cardiac MRI or catheterization of the right heart, or observed outcomes. In the illustrated implementation, the modeling component 16 is implemented as machine readable instructions on a non-transitory computer readable medium, but it will be appreciated that the parameter calculation component can also be implemented as dedicated hardware or a combination of software and dedicated hardware. The results of the model are then provided to an output device 18 configured to provide the calculated parameter to a user in a human comprehensible form. The output device 18 can include one or more of a display, printer, speaker, or other appropriate device capable of providing the parameter representing the right ventricular function of the patient.

The determination of the RVTT and the RVTT/PTT ratio via contrast ultrasound provides a number of advantages. Echocardiography is inexpensive, widely available, and, while it requires some degree of training to perform accurately, there are a reasonably large number of technicians with the necessary training. This convenience allows contrast echocardiography to be readily used for serial measurements. Particularly when compared to cardiac MRI, determining the RVTT via contrast ultrasound takes less time, doesn't require gadolinium-based contrast, which is contraindicated for patients with renal insufficiency, and is freely available to patients with pacemakers, defibrillators, and other implanted devices. Further, the RVTT directly represents the function of the right ventricle, while alternate echocardiographic measures of RV function, such as TAPSE, RV fractional area chance, RV tissue Doppler imaging, or RV strain are either extrapolations of regional measurements to the entire RV or are often limited by the technical quality of the echocardiographic imaging. Even PTT is a relatively non-specific marker of RV pump function as it encompasses additional factors such as pulmonary vascular resistance and the pressure in the left atrium, thus diluting the relevance of these parameters to right ventricular function.

Having a safe, rapid, and reproducible measurement of global RV-pulmonary vascular function, as provided herein, will be of immense value to clinicians when making treatment decisions. The system is relatively straightforward to measure, non-invasive, and utilizes an imaging modality conducive to serial or 'point-of-care' measurements. The applications for echocardiographically derived RVTT and RVTT/PTT are plentiful. Several examples include serial measurements to gauge prognosis and response to treatment of pulmonary hypertension, distinguishing non-invasively PAH from PVH, pre-operative risk stratification (particularly for cardiac surgery), and assessment of RV function in left-heart failure.

In view of the foregoing structural and functional features described above in FIG. 1, example methods will be better appreciated with reference to FIGS. 2-5. While, for purposes of simplicity of explanation, the methods of FIGS. 2-5 are shown and described as executing serially, it is to be understood and appreciated that the present invention is not limited by the illustrated order, as some actions could in other examples occur in different orders and/or concurrently from that shown and described herein.

Figure 2:
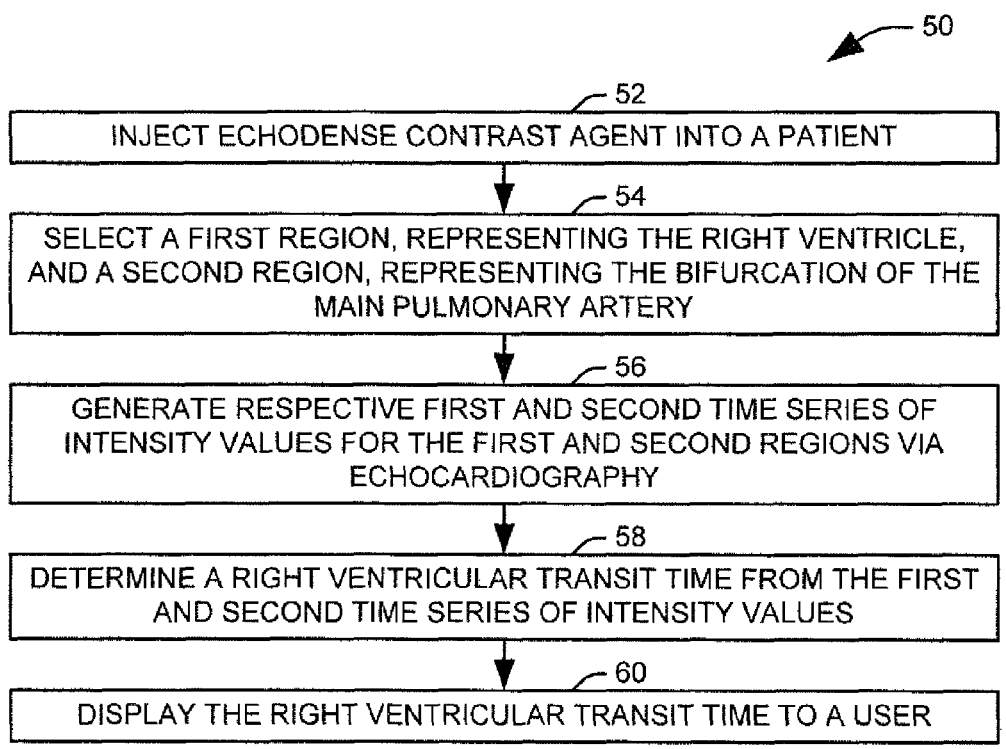
FIG. 2 illustrates one example of a method for determining a right ventricular transit time in accordance with an aspect of the present invention.

FIG. 2 illustrates one example of a method 50 for determining a right ventricular transit time in accordance with an aspect of the present invention. At 52, an echodense contrast agent is injected into a patient, for example, via a peripheral vein. The contrast agent can include any appropriate contrast material for contrast echocardiography. For example, a perflutren lipid microsphere, such as Definity or Optison, can be used. At 54, first and second representative regions are selected, representing the right ventricle of the patient and the bifurcation of the main pulmonary artery, respectively. For example, the first representative region can be selected as a region between one and two millimeters from the coaptation point of the tricuspid valve and centered between the right ventricular free wall and the interventricular septum. In one implementation, a third representative region, representing the left atrium of the patient is also selected.

At 56, respective first and second time series of intensity values for the first and second representative regions are generated via echocardiography. It will be appreciated that, since the echodense contrast agent will increase the intensity of the returned ultrasound signal when it passes through each region, the presence, absence, and relative intensity of the contrast agent at any given time can be effectively determined from these time series. In one implementation, a third time series of intensity values for the third representative region is also generated, representing the passage of the contrast agent through the left atrium.

At 58, the right ventricular transit time is determined from the first and second time series of intensity values. For example, a time interval between a peak intensity in the first time series of intensity values and a corresponding peak intensity in the second time series of intensity values can be determined as the right ventricular transit time. Alternatively, the right ventricular transit time can be determined as a time interval between a first time at which the first time series of intensity values exceeds a first threshold intensity value and a first time at which the second time series of intensity values exceeds a second threshold intensity value. Where the third time series of intensity values is available, a pulmonary transit time can be determined in a similar manner from the first and third time series of intensity values. At 60, the right ventricular transit time is displayed to a user. Where the pulmonary transit time is available, a ratio between the right ventricular transit time and the pulmonary transit time can be calculated as well and displayed to the user. In one implementation, any or all of the right ventricular transit time, the pulmonary transit time, and the calculated ratio can be provided as features to a statistical model configured to evaluate the function of the right ventricle of the patient.

Figure 3:
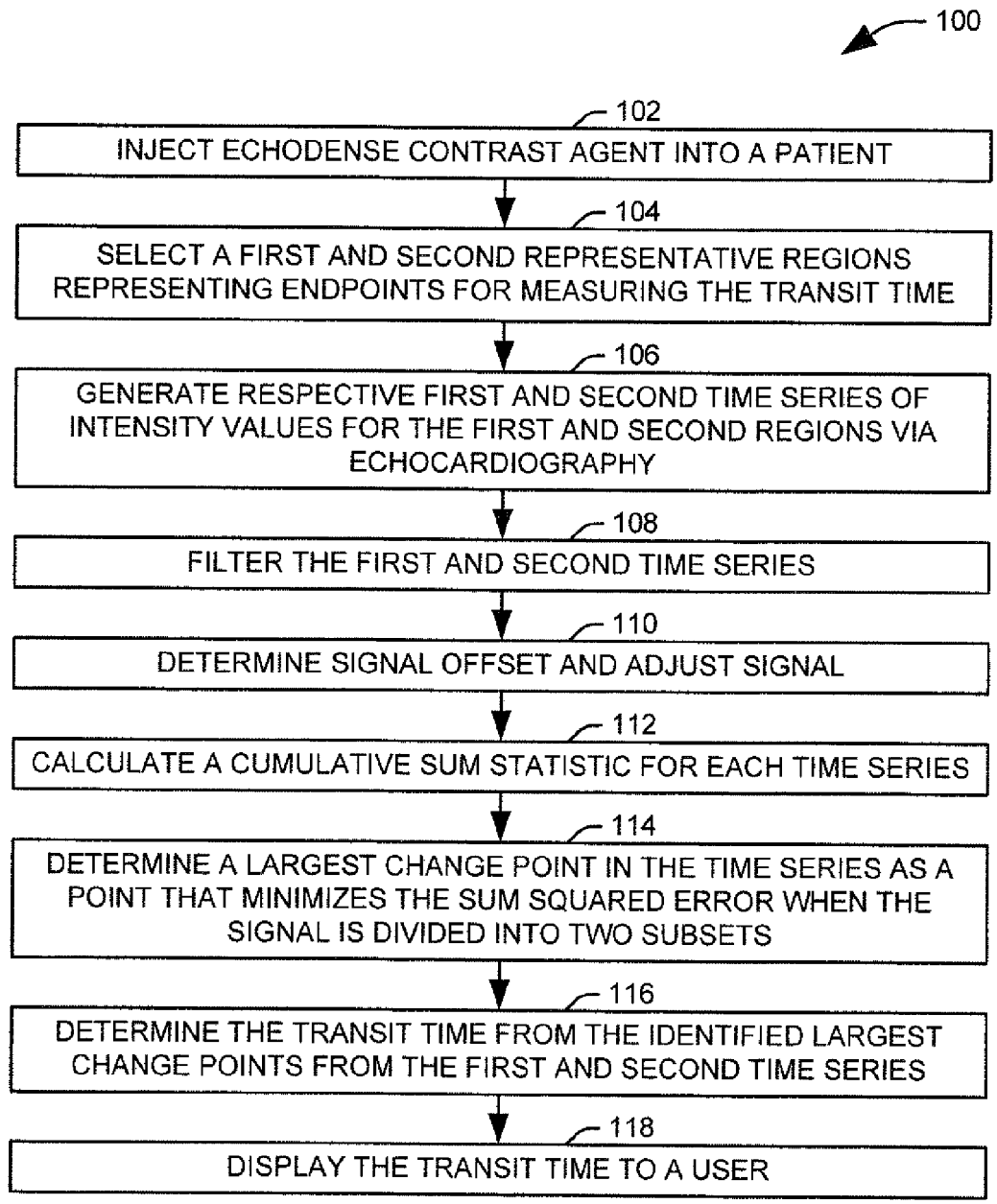
FIG. 3 illustrates one method for determining a transit time via echocardiography in accordance with an aspect of the present invention.

FIG. 3 illustrates one method 100 for determining a transit time via echocardiography in accordance with an aspect of the present invention. At 102, an echodense contrast agent is injected into a patient. At 104, first and second representative regions are selected. For example, where the transit time is a pulmonary transit time, a first representative region could represent a right ventricle of the patient and a second representative region could represent a left atrium of the patient. Where the transit time is right ventricular transit time, a first representative region could represent a right ventricle of the patient and a second representative region could represent a bifurcation of the main pulmonary artery.

At 106, respective first and second time series of intensity values for the first and second representative regions via echocardiography. At 108, the data is filtered, for example, using a Savitzky-Golay filter. At 110, a signal offset is determined and the signal is adjusted to remove the determined offset from all values. In the illustrated implementation, the offset is calculated such that the portion of the signal prior to the introduction of the contrast agent is reduced to approximately zero. At 112, a cumulative sum statistic is calculated. The cumulative sum at a given intensity measurement, $S_i$, is comprised of sequential additions of the difference between the observed signal intensities, and the signal mean, $\bar{I}$, such that:

$$S_i = S_{i-1}(I_i = \bar{I}) \quad \text{Eq. 2}$$

where $I_i$ is an $i^{th}$ intensity measurement in the time series and $S_0 = 0$.

After the cumulative sum statistic is generated for the length of each time series, N, a largest change point for each series, that is, a point at which the signal exhibits a large change associated with the appearance of the contrast at the representative region is determined at 114 by identifying the point m which minimizes the mean squared error, MSE(m) when the signal is divided into two subsets, where:

$$MSE(m) = \sum_{i=1}^{m}\left(I_i - \frac{\sum_{i=1}^{m} I_i}{m}\right)^2 + \sum_{i=m+1}^{n}\left(I_i - \frac{\sum_{i=m+1}^{n} I_i}{n-m}\right)^2 \quad \text{Eq. 3}$$

In one implementation, this point can be verified by inspection by a human operator. If, upon visual inspection, m does not appear to be coincident with the signal onset, for example, if a more abrupt change-point is identified elsewhere, such as on the decay portion of the IDC, the signal subset containing the initial rise is extracted, and the cumulative sum statistic is recalculated on this region. This is repeated until it is confirmed that m corresponds with the appearance of contrast. At 116, the transit time is determined from the largest-change point located in each of the first and second time series of intensity values. The transit time is determined as a time interval between a first time, associated with a largest change point on the first time series of intensity values, and a second time, associated with the a largest change point on the second time series of intensity values. The transit time is displayed to a user at 118.

Figure 4:
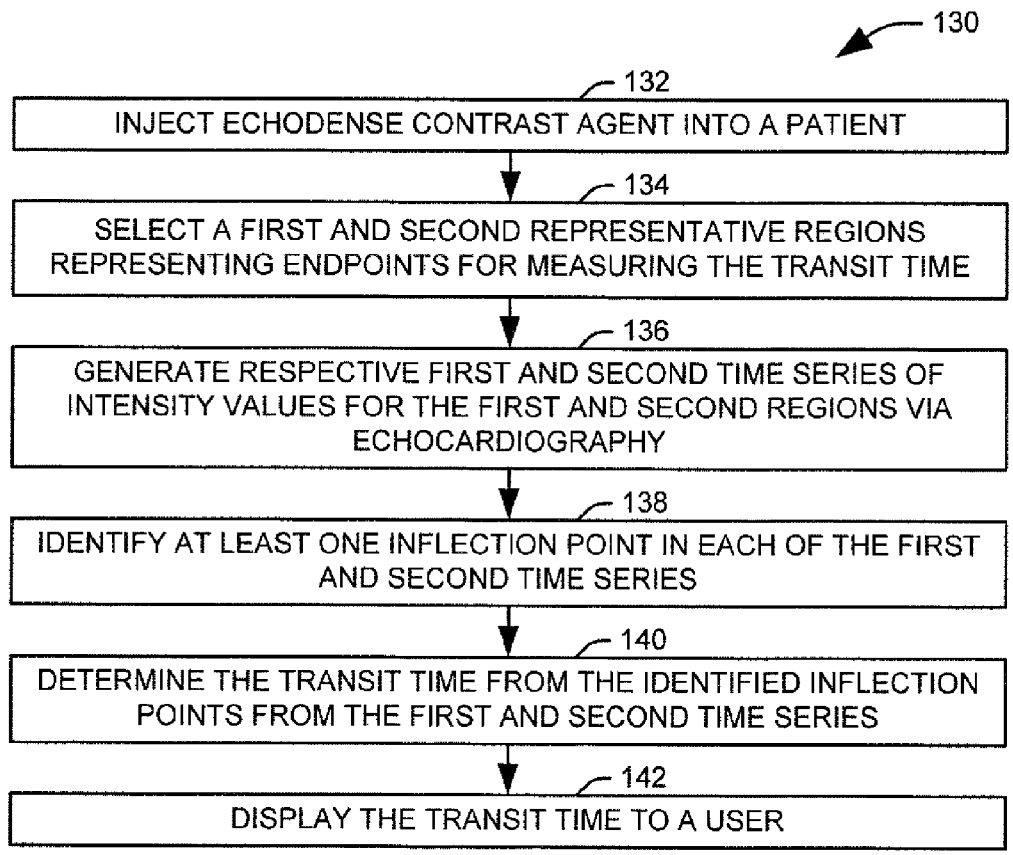
FIG. 4 illustrates another method for determining a transit time via echocardiography in accordance with an aspect of the present invention.

FIG. 4 illustrates another method 130 for determining a transit time via echocardiography in accordance with an aspect of the present invention. At 132, an echodense contrast agent is injected into a patient. At 134, first and second representative regions are selected. For example, where the transit time is a pulmonary transit time, a first representative region could represent a right ventricle of the patient and a second representative region could represent a left atrium of the patient. Where the transit time is right ventricular transit time, a first representative region could represent a right ventricle of the patient and a second representative region could represent a bifurcation of the main pulmonary artery.

At 136, respective first and second time series of intensity values for the first and second representative regions via echocardiography. At 138, at least one inflection point in each of the first and second time series of intensity values is located. At 140, the transit time is determined from the at least one inflection point located in each of the first and second time series of intensity values. For example, representative first and second inflection points, representing an initial rise in signal intensity to their associated time series, can be selected from the at least one inflection points for each time series of intensity values. The transit time is determined as a time interval between a first time, associated with the first representative inflection point, and a second time, associated with the second representative inflection point. The transit time is displayed to a user at 142.

Figure 5:
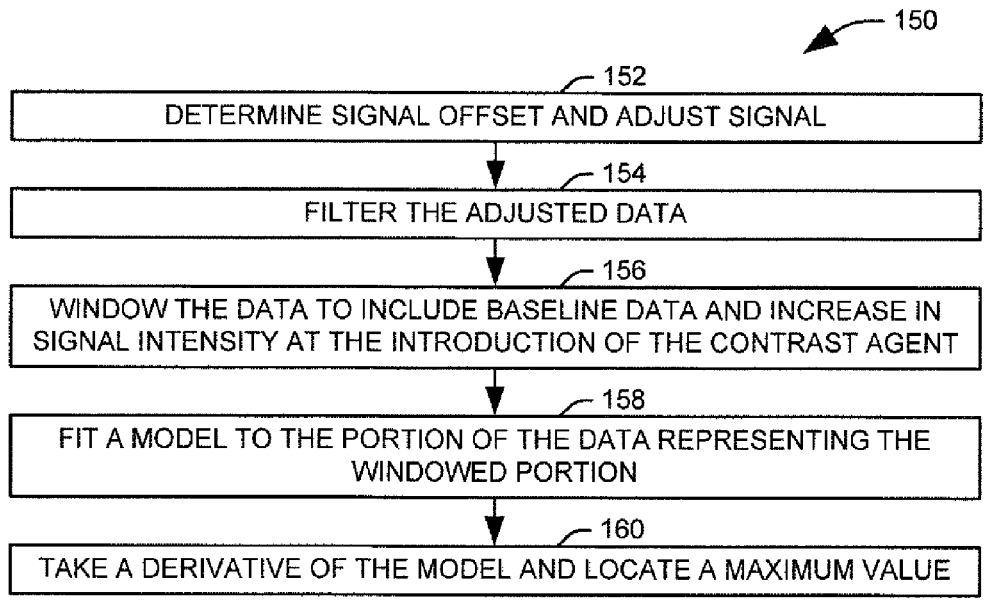
FIG. 5 illustrates a first method for locating inflection points in a time series of intensity values.

FIG. 5 illustrates a first method 150 for locating inflection points in a time series of intensity values. At 152, a signal offset is determined and the signal is adjusted to remove the determined offset from all values. In the illustrated implementation, the offset is calculated such that the portion of the signal prior to the introduction of the contrast agent is reduced to approximately zero. At 154, the data is filtered, for example, using a Savitzky-Golay filter. A Savitzky-Golay filter fits a polynomial of a given order to a frame size of a given number of data points, and in one implementation, a second order polynomial with a frame size of forty-one can be used.

At 156, the data is then windowed to include only the baseline data and a ramp up in signal intensity upon appearance of the contrast agent. The data can be windowed either manually via user input or by an automated program. At 158, a specified model is fit to the portion of the data that describes the rise in signal. In one implementation, the data fitting is performed via a non-linear least squares regression, such as the Levenberg-Marquardt method. In one implementation, the non-linear least squares regression fits the data to a sigmoidal function:

$$I(t) = A + \frac{B}{1 + e^{-Ct+D}} \quad \text{Eq. 4}$$

where I(t) is the time series of intensity values and A, B, C, and D are parameters fit in the regression.

In another implementation, the non-linear least squares regression fits the data to a local-density random walk model:

$$I(t) = \frac{m}{Q}e^{\lambda} \sqrt{\frac{\lambda}{2\pi\mu t}} e^{-\frac{\lambda}{2}\left(\frac{t}{\mu}+\frac{\mu}{t}\right)} \quad \text{Eq. 5}$$

where I(t) is the time series of intensity values and m/Q, $\lambda$, $\mu$ are parameters fit in the regression.

Figure 6:
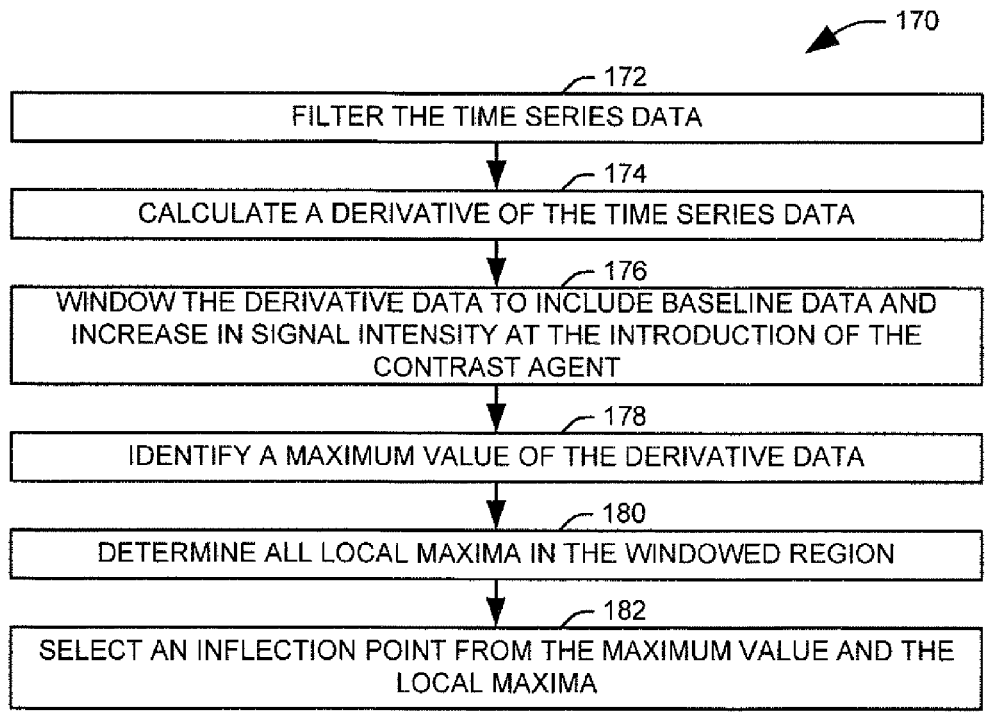
FIG. 6 illustrates a second method for locating inflection points in a time series of intensity values.

At 160, the derivative of the model fit is taken and a maximum of the derivative is located. The maximum value of this derivative corresponds with the inflection point of the signal rise of the model fit, FIG. 6 illustrates a second method 170 for locating inflection points in a time series of intensity values. At 172, the data is filtered, for example, using a Savitzky-Golay filter. At 174, a derivative of the time series is calculated, for example, utilizing an appropriate numerical differentiation algorithm. At 176, the calculated derivative is then windowed to provide a region of interest including only the baseline data and a ramp up in signal intensity upon appearance of the contrast agent. The data can be windowed either manually via user input or by an automated program. At 178, a maximum value of the time-derivative is identified. At 180, all location maxima within the region of interest are determined. For example, a peak-finding algorithm can be employed to locate the local maxima. At 182, an inflection point is selected from the maximum value and the local maxima. In one implementation, the selection is made by a user, but it will be appreciated that an automated process could be used to select the inflection point.

Figure 7:
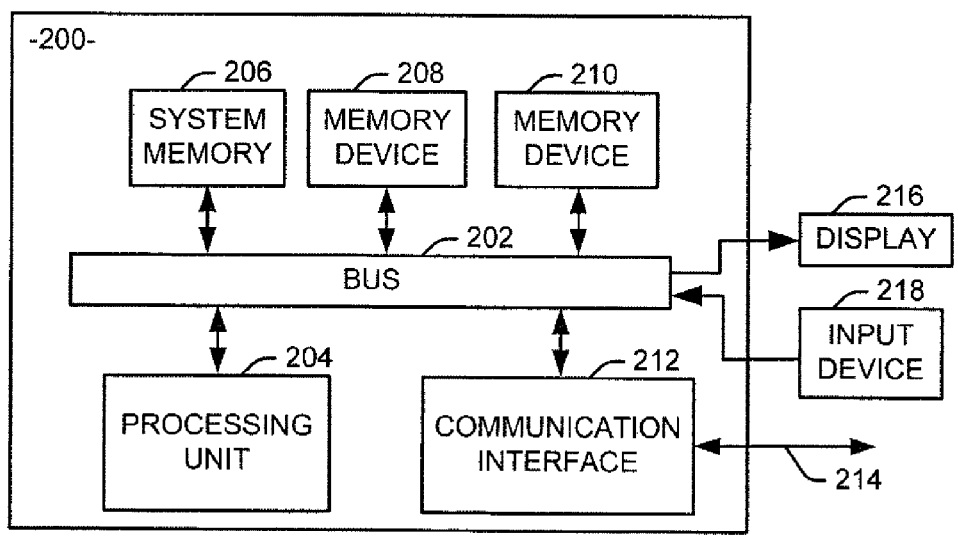
FIG. 7 is a schematic block diagram illustrating an exemplary system of hardware components for implementing the systems and methods described herein.

FIG. 7 is a schematic block diagram illustrating an exemplary system 200 of hardware components capable of implementing examples of the systems and methods disclosed in FIGS. 1-6. The system 200 can include various systems and subsystems. The system 200 can be a personal computer, a laptop computer, a workstation, a computer system, an appliance, an application-specific integrated circuit (ASIC), a server, a server blade center, a server farm, etc.

The system 200 can include a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard and/or a mouse). The system bus 202 can be in communication with the processing unit 204 and the system memory 206. The additional memory devices 208 and 210, such as a hard disk drive, server, stand alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208 and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of a medical diagnostic system in accordance with the present invention. Computer executable logic for determining the right ventricle transit time resides on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to a set of one or more non-transitory media that participate in providing instructions to the processing unit 204 for execution. These media can be local to the process or connected via a local network or Internet connection.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications, and variations that fall within the scope of the appended claims.

What is claimed is:

1. A method for determining a right ventricular transit time for a patient comprising:
    injecting an echodense contrast agent into a patient;
    selecting a first representative region representing a right ventricle of the patient;
    selecting a second representative region representing a bifurcation of the main pulmonary artery;
    generating respective first and second time series of intensity values for the first and second representative regions via echocardiography;
    determining the right ventricular transit time from the first and second time series of intensity values;
    displaying the right ventricular transit time to a user; and
    calculating, with a statistical model, a parameter representing an expected prognosis of the patient from the right ventricular transit time and at least one of a parameter representing systolic function of the left ventricle, a parameter representing diastolic function of the left ventricle, an age of the patient, a sex of the patient, a parameter representing a medical history of the patient, a parameter representing a family history of the patient, a weight of the patient, a height of the patient, and a blood pressure of the patient.

2. The method of claim 1, wherein determining the right ventricular transit time from the first and second time series of intensity values comprises determining a time interval between a peak intensity in the first time series of intensity values and a corresponding peak intensity in the second time series of intensity values.

3. The method of claim 1, wherein determining the right ventricular transit time from the first and second time series of intensity values comprises determining a time interval between a first time at which the first time series of intensity values exceeds a first threshold intensity value and a first time at which the second time series of intensity values exceeds a second threshold intensity value.

4. The method of claim 1, wherein determining the right ventricular transit time from the first and second time series of intensity values comprises:
    determining a first time associated with a first inflection point, representing a rise in signal intensity, from a first time series of intensity values;
    determining a second time, associated with a second inflection point, representing a rise in signal intensity, from a second time series of intensity values; and
    determining a time interval between the first time and the second time.

5. The method of claim 4, wherein determining the first time associated with the first inflection point comprises:
    identifying a portion of the first time series of intensity values representing a rise of signal intensity above a determined baseline;
    fitting a model to the identified portion of the first time series of intensity values to provide a time-dependent function; and
    determining the inflection point at a point at a local maximum of the derivative of the time-dependent function.

6. The method of claim 5, wherein fitting the model to the identified portion of the first time series of intensity values comprises fitting a local-density random walk model to the identified portion of the first time series of intensity values.

7. The method of claim 5, wherein fitting the model to the identified portion of the first time series of intensity values comprises fitting a sigmoidal model to the identified portion of the first time series of intensity values.

8. The method of claim 4, wherein determining the first time associated with the first inflection point comprises:
    calculating a derivative of the first time series of intensity values;
    windowing the calculated derivative to a region of interest;
    identify all local maxima in the region of interest; and
    selecting the first time associated with the first inflection point from times associated with the identified local maxima.

9. The method of claim 1, selecting the first representative region representing the right ventricle of the patient comprises selecting a region between one and two millimeters from the coaptation point of the tricuspid valve and centered between the right ventricular free wall and the interventricular septum.

10. The method of claim 1, further comprising:
    selecting a third representative region representing a left atrium of the patient;
    generating a third time series of intensity values for the third representative region via echocardiography; and
    determining a pulmonary transit time from the first and third time series of intensity values.

11. The method of claim 10, further comprising calculating a ratio of the right ventricular transit time to the pulmonary transit time.

12. The method of claim 1, further comprising providing the right ventricular transit time as a feature to a statistical model configured to evaluate a function of the right ventricle of the patient.

13. A method comprising:
determining, at each of a first time and a second time, a right ventricular transit time for a patient, wherein determining a right ventricular transit time comprises:
injecting an echodense contrast agent into a patient;
selecting a first representative region, representing a right ventricle of the patient, and a second representative region, representing a bifurcation of the main pulmonary artery;
generating respective first and second time series of intensity values for the first and second representative regions via echocardiography;
locating at least one inflection point in each of the first and second time series of intensity values;
determining the right ventricular transit time from the at least one inflection point located in each of the first and second time series of intensity values; and
displaying the transit time to a user;
providing a medical treatment to the patient between the first time and the second time; and
comparing the determined right ventricular transit time at the second time to the determined right ventricular transit time at the first time to evaluate a response of the patient to the medical treatment.

14. The method of claim 13, wherein locating the at least one inflection point in each of the first and second time series of intensity values comprises:
identifying a portion of the each time series of intensity values representing a rise of signal intensity above a determined baseline;
fitting a model to each identified portion to provide respective first and second time-dependent functions;
determining an inflection point of the at least one inflection point for the first time series of intensity values at a point at a local maximum of the derivative of the first time-dependent function; and
determining an inflection point of the at least one inflection point for the second time series of intensity values at a point at a local maximum of the derivative of the second time-dependent function.

15. The method of claim 14, wherein fitting the model to each identified portion comprises fitting a local-density random walk model to the identified portion.

16. The method of claim 14, wherein fitting the model to each identified portion comprises fitting a sigmoidal model to the identified portion.

17. The method of claim 13, wherein locating the at least one inflection point in each of the first and second time series of intensity values comprises:
calculating a derivative of each of the first and second time series of intensity values;
windowing each calculated derivative to respective first and second regions of interest; and
identify all local maxima in each region of interest.

18. The method of claim 17, wherein determining the transit time from the at least one inflection point located in each of the first and second time series of intensity values comprises:
selecting a first inflection point, representing an initial rise in signal intensity, from the identified local maxima of the first region of interest;
selecting a second inflection point, representing an initial rise in signal intensity, from the identified local maxima of the second region of interest; and
determining the transit time as a time interval between a first time, associated with the first inflection point, and a second time.

19. A method for determining a right ventricular transit time for a patient comprising:
injecting an echodense contrast agent into a patient;
selecting a first representative region and a second representative region;
generating respective first and second time series of intensity values for the first and second representative regions via echocardiography;
locating a point of largest change in each of the first and second time series of intensity values, the point of largest change representing a time, m, that minimizes the following function of m, calculated as a mean squared error (MSE):

$$MSE(m) = \sum_{i=1}^{m}\left(I_i - \frac{\sum_{i=1}^{m} I_i}{m}\right)^2 + \sum_{i=m+1}^{n}\left(I_i - \frac{\sum_{i=m+1}^{n} I_i}{n-m}\right)^2$$

where n is an number of intensity values in a given time series and $I_i$ is an $i^{th}$ intensity value in the given time series;
determining the right ventricular transit time from the point of largest change located in each of the first and second time series of intensity values; and
displaying the right ventricular transit time to a user.

* * * * *